United States Patent [19]

Strobel

[11] 4,132,774
[45] Jan. 2, 1979

[54] METHOD OF AND COMPOSITION FOR SCREENING ERYTHEMA INDUCING ULTRAVIOLET BANDS

[75] Inventor: Albert F. Strobel, Delmar, N.Y.

[73] Assignee: GAF Corporation, New York, N.Y.

[21] Appl. No.: 747,598

[22] Filed: Dec. 6, 1976

[51] Int. Cl.$^2$ ............................................... A61K 7/44
[52] U.S. Cl. ...................................... 424/60; 424/174
[58] Field of Search ................................. 424/60, 310

[56] References Cited

U.S. PATENT DOCUMENTS

| | | | |
|---|---|---|---|
| 2,340,776 | 2/1944 | Stambovsky | 424/310 X |
| 3,403,207 | 9/1968 | Kreps et al. | 424/60 |
| 3,479,428 | 11/1969 | Bryce et al. | 424/59 X |

*Primary Examiner*—Dale R. Ore
*Attorney, Agent, or Firm*—Walter C. Kehm; Marilyn J. Maue

[57] ABSTRACT

A novel sun tanning composition, method of making same and method of controlling sunburn comprising application to the skin of a cosmetic carrier containing the novel mixture of ethyl esters of N-monoalkylamino and N,N-dialkylamino benzoic acid wherein the alkyl groups are methyl or ethyl and the amino and ester groups are in para relationship on the benzene ring.

15 Claims, No Drawings

METHOD OF AND COMPOSITION FOR SCREENING ERYTHEMA INDUCING ULTRAVIOLET BANDS

The present invention is directed to liquid products and compositions adapted for application to the human skin for protection against erythema producing radiation.

Extensive studies have shown that, of the ultraviolet radiation of sunlight on the human skin, i.e. the radiation between 300 m$\mu$ and 318 m$\mu$, produces substantially all of the erythemal energy and burning portion of the energy, while that between 320 and 360 m$\mu$ promotes tanning. The differing intensities and the erythemal and tanning effectiveness of the various wave lengths within these ranges have been established and methods have been determined for calculating accurately their effects on normal untanned skin.

Normal untanned and unprotected skin may be exposed safely to noon-time summer sunlight only for a comparatively limited period. Ultraviolet screens are provided for the purpose of extending that exposure time and are generally evaluated on a basis of an exposure time of from 1 to 4 hours. The total erythemal flux of noon-day summer sun during these periods is limited by an ultraviolet screen designed to provide the desired degree of protection and tanning with safety over extended periods.

A practical, all-purpose sun-tanning composition should provide high screening efficiency in the erythemal area coupled with high transmission of incident tanning energy; be capable of being readily incorporated in the various media used to apply them to human skin, and remain stable, effective and cosmetically acceptable therein under all conditions normally encountered in commercial use; form a thin, continuous, long-lasting protective film on the skin; and be resistant to oxidation by air and stable on exposure to both ultraviolet and visible radiation under all normal conditions of storage, application and use.

For human application, ultraviolet screens are incorporated in various media; hydroalcholic lotions, oily solutions, gels and water and oil lotions and creams. Additionally, a material such as dihydroxyacetone may be incorporated in the medium to provide an artificial "tanning" with ultraviolet protection, i.e. pigmentation of the skin which resembles natural melanin pigmentation in appearance only. The principal objective of this invention is to provide a new and improved composition capable of satisfying all of the requirements for a modern, all-purpose, commercially acceptable, ultraviolet sun-tanning composition for application to the human skin.

It has been known that various amino benzoic acid derivatives have good sun screening properties. In particular, the individual N,N-dimethylamino and N,N-diethylamino benzoates having 5 to 18 carbon atoms in the ester moiety are disclosed in British Pat. No. 1,162,337 and similarly in U.S. Pat. No. 3,403,207. However, these particular esters do not provide adequate sun screening properties unless heavy applications on the skin are employed. Also such applications are unfeasible from the standpoint of economy. Moreover, certain members of this group are solid at room temperatures, e.g. dodecyl-p-(N,N-dimethylamino) benzoate has a melting point of 50° C., which tends to cause separation from liquid carriers and flaking on the skin under normal conditions of use. Others, e.g. oleyl dimethylamino benzoate, possess an undesirable deep yellow color and oily consistency which is objectionable from a cosmetic standpoint.

Also certain undesirable properties of the individual methyl, ethyl, propyl and butyl esters of N,N-dimethylamino and N,N-diethylamino benzoic acids are described in U.S. Pat. No. 2,853,423.

Although all of the above-discussed compounds possess some ability to screen out certain portions of UV light in the 300 to 360 range, they lack one or more essential characteristics of a good sun tanning compound such as insolubility in water, nonstaining of fabrics, stability on storage, stability on exposure to ultraviolet or visible radiation, resistance to oxidation by air, solubility in cosmetic carriers at low temperatures and the ability to resist caking and flaking on the skin. Furthermore, many do not have sufficiently low melting points to remain in the liquid state at skin temperature, are not self-plasticizing and are not compatible with common ingredients of suntan lotions, such as dihydroxyacetone. The present invention is intended and adapted to improve sun screening products of the alkylaminobenzoate type, it being among the objects thereof to provide compositions which have high screening efficiency which are transparent to the tanning rays, have marked solubility in or miscibility with such materials as lower alcohols, mineral vegetable and animal oils, and are stable as liquids on exposure in thin films to both air and light simultaneously.

It is further among the objects of the invention to provide substances for the above purpose which are stable on storage, which do not stain fabrics, which are nonreactive with constituents of cosmetic carriers, which have low melting points and are self-plasticizing, and which have little tendency to crystallize from compositions used as sun screening preparations.

According to the present invention, there is provided mixtures of p-ethyl esters of N-mono- and N,N-dimethylamino- and/or ethylamino- benzoic acids in critical concentration wherein the N,N-dialkylamino ethylbenzoate portion is between about 25 and 50 weight % for the N,N-dimethylamino-p-ethylbenzoate in a bicomponent mixture, and between about 50 and 85 weight % of the mixture for N,N-diethylamino-p-ethylbenzoate in a bi-component mixture; and wherein the N-monoethylamino- and N,N-diethylamino- ethylbenzoate mixture can contain the N-monomethylamino- and N,N-dimethylamino- ethylbenzoate mixture in a four component mixture. The benzoate components of the present mixtures can be defined by the following chemical structure:

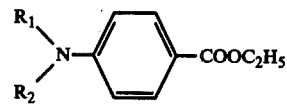

wherein $R_1$ is methyl or ethyl and $R_2$ is methyl, ethyl or hydrogen. Preferred of the dialkylaminoalkyl benzoate group are those wherein $R_1$ and $R_2$ represent the same alkyl radical.

Particularly preferred are the 40–50 weight % N,N-dimethylaminobenzoic ethyl ester and 50–60 weight % N-monomethylamino benzoic ethyl ester bicomponent mixture; the 75–85 weight % N,N-diethylamino benzoic ethyl ester and 15–25 weight % N-monoethylamino benzoic ethyl ester bi-component mixture; and the above N,N-diethylamino-p-ethyl benzoate/N-monoethylamino-p-ethylbenzoate containing the corresponding methyl substituted amino-p-ethylbenzoate pair in an amount up to 50 weight %, most preferably up to 30 weight %, of the total benzoate mixture, to provide a 4-component mixture of benzoates.

It is to be understood that bi-component mixtures of N,N-diethylamino-p-ethylbenzoate with N-methylamino-p-ethylbenzoate or mixtures of N,N-dimethylamino-p-ethylbenzoate with N-ethylamino-p-ethylbenzoate can also be employed provided that the concentrations of the dialkylamino ethyl benzoate portions are observed. Also, tri-component mixtures of the N,N-diethylamino and N-monoethylamino- ethylbenzoate with either the N,N-dimethylamino- or the N-monomethylamino- ethylbenzoate can be employed, as well as the tri-component mixtures of the N,N-dimethylamino- and N-monomethylamino- ethylbenzoate with either the N,N-diethylamino- or the N-monoethylamino-ethylbenzoate, provided the concentration of the respective dialkylamino ethylbenzoate is within the critical ranges set forth above.

The alkylamino ethylbenzoate mixtures of the present invention, hereinafter referenced as "the benzoate mixtures", are generally applied as formulations which may be prepared by incorporation in a vehicle in a concentration between about 0.5 and 12 weight %, preferably between about 1 and about 5 weight %, of the total composition. Additionally, from about 0.1 to about 8 weight %, preferably from about 0.5 to about 5 weight %, of the total formulation of stabilizing agents or antioxidants, such as nordihydroguiaretic acid, butylated hydroxy anisole, butylated hydroxytoluene, 2,6-di-tert-butyl-4-alkylphenol, ascorbic acid, citric acid, hydroquinone and dilaurylthiodipropionate can be incorporated in the final composition as well as insect repellant additives and perfume additives in about the same concentration.

Suitable vehicles for the benzoate mixtures include those conconventionally employed, e.g. $C_2$ to $C_4$ monohydroxy alcohols; glycols; mineral, vegetable or animal oils, water; glycerine; polysiloxanes; esters of higher aliphatic acids, such as mono- and poly- hydricalcohol esters of capric, lauric, myristic, palmitic, stearic, citronellic, oleic, azelaic and sebacic acid; low molecular weight liquid polymers; and mixtures thereof such as for example, water-alcohol mixtures, glycerine-alcohol mixtures, water and oil cream mixtures, oil based lotions, commercial formulations for cosmetic purposes and any of those mixtures set forth in the following Examples.

Individually, $C_1$ to $C_4$ alkyl esters of diethylamino- and dimethylamino- benzoic acids are solids at normal atmospheric temperatures (i.e. up to about 100° F.). Accordingly, these esters, when individually employed, tend to cake on the skin and flake, leaving the skin unprotected.

Since sun screening preparations are generally used in hot weather and at beaches where people enjoy bathing, it is essential that a thin layer of protective coating on the skin not be appreciably affected by water or perspiration. The present mixtures which form liquid films on the skin, unlike the individual components which are solids, cannot be easily brushed off or flushed away by contact with water.

Aditionally the individual $C_1$ to $C_4$ esters of aminobenzoic acid are appreciably insoluble in mineral, vegetable and animal oils at ambient temperature. Even at concentrations as low as 1% in mineral oil the individual methyl, ethyl and propyl esters separate out immediately at room temperature, while the butyl ester separates from the oily vehicle within 24 hours and slowly crystalizes.

Surprisingly, it is now discovered that by providing the present benzoate mixtures, the melting point of the composite is appreciably lower than that of any of the individual components. Significantly, the melting points of the benzoate mixtures herein defined are below 30° C. as compared with the melting point of 45° C. for ethyl-p-(N,N-dimethylamino) benzoate and 67°-68° C. for ethyl-p-(N,N-diethylamino) benzoate. Hence, the benzoate mixtures of the present invention are ideally suitable for use in volatile liquid sprays, as well as in emollients and creams which are capable of providing a moisturizing effect by deposition of a thin protective liquid film on the skin. The present benzoate mixtures are also miscible with oils so that separation or crystallization from emulsions is avoided.

Low solubility of these mixtures in water also avoids easy removal by perspiration and sea bathing while their clear, colorless nature enhances their cosmetic properties.

Of great importance is the radiation absorption range of instant benzoate mixtures. Their absorption curves show maxima in the 305 to 315 mμ range and drop off sharply above 320 mμ so that at 340 mμ, absorption is less than 15% of maximum.

The mixtures have high absorptivities at the maxima: $K_{max} = 148$ for

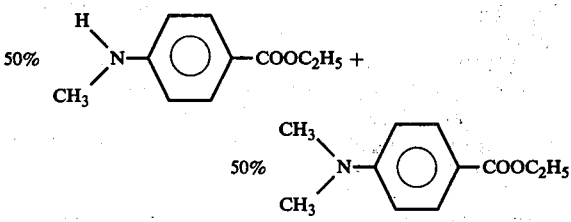

$K_{max} = 142$ for

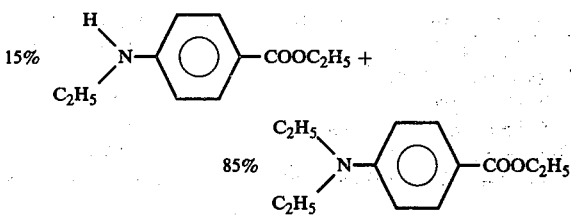

By contrast, amyl-p-(N,N-dimethyl)benzoate of the formula

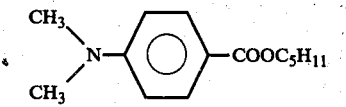

has a Kmax of 117.8. The higher alkyl esters have even lower K values. Thus the mixtures of the present invention not only have the desirable liquid feature, but also have greater strength than the corresponding $C_{5+}$ esters heretofore employed. Consequently, these benzoate mixtures are superior in preventing sun burning while offering no barrier to tanning rays of the sun.

The present benzoate mixtures can be conveniently prepared by physically combining the individual species within the above critical limits. Also, the mixtures can be obtained directly in mixture by gradual addition of ethyl-p-aminobenzoate to a molar excess of dimethyl- or diethyl- sulfate, preferably with constant agitation, for a period of 0.25 to 5 hours, preferably from 0.5 to 2 hours, at a temperature between about 35° C. and about 80° C. under ambient pressure. Mole ratios of dialkylsulfate : ethyl aminobenzoate between about 5:1 to 1.5:1, preferably between 3:1 and 1.8:1, are beneficially employed. The mixture is then reacted at from about 50° to about 120° C., preferably from 60° to 100° C. for 0.5 to 5 hours after which it is cooled below reaction temperature, e.g. between 30° to 50° C., and an inert monocyclic aromatic compound, such as benzene, xylene, or toluene, is added in an amount from about 30% up to about 60% by weight, preferably 45 to 50% by weight, of the mixture to dissolve the product of the reaction therein. Water is then added in an amount of from about 30% up to about 60% by weight, preferably 45% to 50% by weight, to dissolve the carbonate and reaction by-product of the reaction and the pH of the diluted mixture is adjusted to the alkaline side, preferably between about 8 and about 10 by addition of a carbonate of sodium or potassium. Upon the addition of water, two distinct liquid layers are formed, namely a lower aqueous layer containing by-product and an upper organic layer containing product. The aqueous layer is separated and the organic layer is distilled to remove any remaining water and monocyclic aromatic compound. The distilland, containing some solvent and the benzoate mixture, is treated with additional dialkyl sulfate and the resultant $HSO_3OR$ by-product is neutralized by addition of water, monocyclic aromatic compound and carbonate salt. The water layer is drawn off and the solvent is distilled from the organic layer as above. The remaining crude benzoate mixture is then distilled under vacuum to provide the essentially colorless benzoate mixture of the present invention. Addition of 0.1 to 2 weight % antioxidant, e.g. 2,6-di-tert-butyl-4-methylphenol, is recommended to insure color stability.

Generally, the boiling range of the present benzoate mixtures falls within the range of 100° to 150° C. at 5 mm Hg.; more particularly, the mono- and di- methylated amino ethylbenzoate pair boils within the range of 120° to 130° C. at 5mm Hg. and the mono- and di- ethylated amino ethylbenzoate pair boils within the range of 130° to 140° C. at 5 mm Hg.

The invention is now illustrated by the following examples which are set forth to provide preferred embodiments of the present invention, but which are not to be construed as limiting to the scope of the invention as defined in the foregoing disclosure and the claims. All amounts and proportions in the following examples are by weight unless otherwise specified.

EXAMPLE 1

To 924 g (6 moles) of diethyl sulfate contained in a 3-necked flask equipped with condenser, thermometer, and stirrer, is added under an atmosphere of nitrogen, 495 g (3 moles) of ethyl p-aminobenzoate in four portions. After addition of the first portion, the reaction mixture is stirred for 0.5 hour at 60° C. After addition of each of the remaining portions, the reaction mixture is stirred for 0.75 hr. at 60° C. The mixture is heated at 80° C. for two hours and then cooled to 30° C.

Water (750 ml) and benzene (600 ml) are then added, and the resulting mixture is made alkaline to Brilliant Yellow paper by the addition of sodium carbonate. An additional amount of water (600 ml) is added, and the resulting two layers were separated. Benzene is distilled from the organic layer, and to liquid remaining 90 g (0.58 mole) of diethyl sulfate is added. The mixture is stirred for two hours at 80° C. and then cooled to 30° C. Additional water (1350 ml) and benzene (300 ml) are added, and the resulting mixture is again made alkaline to Brilliant Yellow paper with sodium carbonate. After the addition of another 30 g of sodium carbonate, the mixture is refluxed for four hours and then cooled. The resulting two layers are separated, and 1350 ml of water and 30 g of sodium carbonate is added to the organic layer. The mixture is refluxed for four hours, the two liquid layers are separated, and benzene is distilled from the organic layer. The remaining liquid is distilled at 5 mm after which 652 g of the following mixture, which has a K value of 141.7 and a boiling range of 135° to 138° C. at 5 mm Hg. is collected.

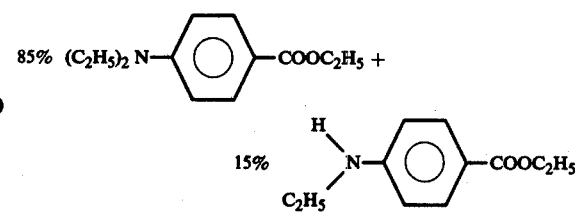

EXAMPLE 2

To 252 g (2 moles) of dimethyl sulfate contained in a three-necked flask equipped with condenser, thermometer and stirrer is added under nitrogen, 165 g (1 mole) of ethyl p-aminobenzoate in four portions. After addition of the first portion, the reaction mixture is stirred at 60° C. for 0.5 hr. After addition of each of the remaining portions, the mixture is stirred for 0.75 hr. at the same temperature. The mixture is then heated at 80° C. for two hours, after which it is cooled to 30° C. and 250 ml of water and 200 ml of benzene is added. The mixture is made alkaline with sodium carbonate until the solution gives an orange color on Brilliant Yellow test paper. Another 32.5 g of sodium carbonate and 200 ml of water is then added, and the resulting mixture refluxed for four hours. The resulting two liquid layers are then separated, and benzene distilled from the organic layer at 50 mm Hg pressure. The remaining liquid is distilled at 5 mm to give 152 g of the following mixture which has a K value of 148.8 and a boiling range of 125° to 128° C. at 5 mm Hg.

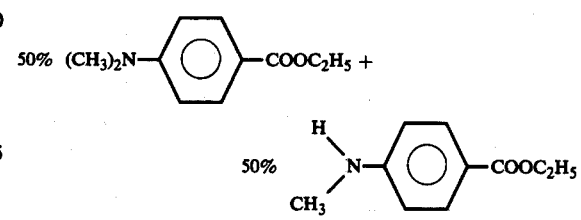

EXAMPLE 3

The mixture of Example 1 is combined with 30% by weight of the mixture of Example 2 to give a 4 component liquid mixture.

EXAMPLE 4

Sun tan lotions are prepared by combining three separate solutions of 65 parts by weight ethyl alcohol with each of 35 parts by weight of the products of Examples 1, 2 and 3. Each of the separate lotions are then applied to the skin in separate tests and exposed to strong midday sunlight for a period of 0.5 hour. The alcoholic vehicle volatilizes within a few minutes leaving a smooth colorless continuous film of the benzoate mixtures on the skin. After 0.5 hours, no crystallization occurs and an adherent, continuous and colorless liquid film of each of the present mixtures remains on the skin to provide lasting protection against the burning rays of the sun while permitting tanning rays to penetrate.

The preparation of the sun tan lotion of Example 4 is repeated except that the products of Examples 1, 2 or 3 is replaced with individual components of the benzoate mixture, namely the ethyl ester of p-(N,N-dimethylamino) benzoic acid and the ethyl ester of p-(N-diethylamino) benzoic acid. In both cases after evaporation of the alcoholic vehicle, the ethyl esters individually incorporated, crystallize on the skin and are easily removed by flaking off.

EXAMPLE 5

The preparation of the sun tan lotion of Example 4 is repeated except that the products of Examples 1, 2 and 3 are replaced with benzoate mixtures outside the critical ranges of the present invention. In test 5A the benzoate mixture consists of 10 weight % of ethyl-p-(N-ethylamino) benzoate and 90 weight % of ethyl-p-N,N-diethylamino) benzoate. In test 5B the benzoate mixture consists of 80 weight % of ethyl-p-(N-ethylamino) benzoate and 20 weight % of ethyl-p-(N,N-diethylamino) benzoate.

In test 5C the benzoate mixture consists of 85 weight % ethyl-p-(N-methylamino) benzoate and 15 weight % ethyl-p-(N,N-dimethylamino) benzoate, and in test 5D the benzoate mixture consists of 30 weight % ethyl-p-(N-methylamino) benzoate and 70 weight % ethyl-p-(N,N-dimethylamino) benzoate.

When the compositions of tests 5B and 5C are applied to the skin, yellowing occurs which is not only objectionable from a cosmetic standpoint, but causes staining of clothing in contact with the formulation.

In the case of compositions of tests 5A and 5D, the benzoate mixture crystallizes on the skin and is easily removed by abrasion or is flushed off; thus providing no protection against sun burn.

EXAMPLE 6

A two percent solution of the product of Example 1 in ethanol is compared with a two percent solution of pentyl-p-(N,N-dimethylamino) benzoate by separately applying both solutions to the back area of human panelists. The panelists are exposed to Florida midday sun for 3.5 hours at an average temperature of 83° F. Five days after exposure it is found that the areas protected by the product of Example 1 shows 76% reduction in skin peeling over nonprotected areas; whereas the areas protected by pentyl-p-(N,N-dimethylamino) benzoate shows only 53% reduction in skin peeling. It is also noted that the sample containing the pentyl benzoate developed a disagreeable odor after use which odor is absent from the samples containing benzoate mixtures of Examples 1, 2 and 3. The above test is repeated, except that homomenthyl-salicylate is substituted as the sun screening agent. Under the same conditions only 12% reduction in skin peeling is found for this agent.

EXAMPLE 7

A one-ounce sample of each of the products of Examples 1, 2 and 3 are separately combined with 32 ounces of polyoxyethylated vegetable oil. Each of these preparations results in clear solutions which remain liquid when applied to the skin and affords complete protection against sunburn and windburn after 4 hours exposure to strong midday sunlight at an average temperature of 85° F.

Separate one-ounce samples of each of the products of Examples 1, 2 and 3 in 32 ounces of polyoxyethylated vegetable oil fail to show any signs of precipitation after storage for one month at ambient temperatures. Thus, sun screening preparations made with the present benzoate mixtures provide good shelf life.

EXAMPLE 8

The water solubility of the present benzoate mixtures is shown in the following table where one-ounce samples of the following mixtures are added to water at room temperature.

| SAMPLE | % SOLUBILITY |
|---|---|
| Mixture of Example 1 | substantially insoluble (less than 0.5%) |
| Mixture of Example 2 | substantially insoluble (less than 0.5%) |
| Mixture of Example 3 | substantially insoluble (less than 0.5%) |

EXAMPLE 9

A 2% solution of each of the products of Examples 1, 2 and 3, are prepared in a 50:50 mixture of alcohol-glycerin and each is separately applied to the skin and allowed to dry. Skin so treated does not develop a burn after exposure to sunlight for 4 hours at an average day temperature of 85° F.

EXAMPLE 10

One ounce of each of the products of Examples 1, 2 and 3 is separately combined with a liquid mixture of 32 oz. of isopropyl stearate and 15 oz. polyoxyethylated sorbitan monopalmitate (Tween 40) to form a paste. This material when applied to the skin and allowed to dry, affords protection against sunburn, under conditions set forth in Example 7. In addition, the formulation provides a moisturizing effect on the skin.

EXAMPLE 11

Three separate and equal samples of a sun tanning vehicle are prepared as follows. A mixture of 6 parts of mineral oil and 7 parts of stearic acid are heated to 75° C. and added with stirring to a heated (75° C.) mixture of 70 parts of water, 3 parts of glycerin, 2.5 parts of triethanolamine, and 2 parts of sodium alginate. To the resulting emulsion of each sample there is added while hot (65° C.) 2.5 parts of the individual samples of each of the products of Examples 1, 2 and 3 dissolved each in 7.0 parts of coconut oil. An excellent smooth lotion results which affords protection against sunburn under the conditions of Example 7.

EXAMPLE 12

The mixtures of Examples 1, 2 and 3 are incorporated separately into a cosmetic cream at 2% (by weight) concentration. The cream is composed of:

| | |
|---|---|
| petrolatum | 9.0 parts |
| mineral oil | 4.0 parts |
| water | 62.0 parts |
| glyceryl monostearate | 6.0 parts |
| beeswax | 3.5 parts |
| polyvinylpyrrolidone | 2.0 parts |

In addition to providing protection against sun burn under the intense conditions set forth above in Example 7, the cream affords a moisturizing effect on the skin.

EXAMPLE 13

The following liquid cream formulations are prepared using the sun tanning agents indicated:

| | weight % | weight % | weight % |
|---|---|---|---|
| Water Phase | | | |
| Carbopol 934[5] | 0.75 | 0.75 | 0.75 |
| Distilled H$_2$O | 75.25 | 75.25 | 75.25 |
| Dowicil 200[6] | 0.10 | 0.10 | 0.10 |
| 10% aq. Solns. of | | | |
| NaOH and | 2.25 | 2.25 | 2.25 |
| Ethomeen C-25[1] | 3.65 | 3.65 | 3.65 |
| Oil Phase | | | |
| Amerchol L-101[2] | 5 | 5 | 5 |
| Modulan[3] | 5 | 5 | 5 |
| Solulan 16[4] | 1 | 1 | 1 |
| Petrolatum U.S.P. | 5 | 5 | 5 |
| Sun tan Agent A | 2 | — | — |
| Sun tan Agent B | — | 1 | — |
| Sun tan Agent C | — | — | 1.5 |

Sun tan agent A is amyl-p-N,N-dimethylamino benzoate;
Agent B is a mixture of 80% ethyl-p-N,N-diethylaminobenzoate and 20% ethyl-p-N-ethylaminobenzoate and Agent C is homomenthylsalicylate.

[1] A tertiary aliphatic amine having a C$_{25}$ chain length, supplied by Armak Chemicals in Rutherford, New Jersey
[2] A lanolin derived sterol extract, supplied by Amerchol, Edison, New Jersey
[3] A lanolin acetate emollient, supplied by Amerchol, Edison, New Jersey
[4] Ethoxylated lanolin alcohols, supplied by Amerchol, Edison, New Jersey
[5] Acrylic acid polymer with sucrose polyallyl ether, supplied by B. F. Goodrich Chemical Co., Ohio
[6] 1-(3-chloro-2-propenyl)-3,5,7-triaza-1-azoniatricyclo [3.3.1 3.7] decane chloride, supplied by Dow Chemical Co., New Jersey Based on testing of 6 panelists in strong mid-day sun at 85° F. for an average exposure time of 2.75 hours, the formulation containing Agent A effects a 50% reduction on the incidence of peeling; Agent B effects a 75% reduction and Agent C effects only 10% reduction.

Having thus described my invention, I claim:

1. A sun screening composition comprising an inert carrier having distributed therein an effective sunscreening amount of a mixture of N-monoalkylamino- and N,N-dialkylamino-ethylbenzoates having the structure

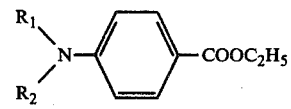

wherein $R_1$ is methyl or ethyl and $R_2$ is hydrogen, methyl or ethyl, and intermixtures thereof; and wherein the N,N-dialkylamino ethylbenzoate portion of the mixture is between about 25 and 50 weight % where $R_1$ and $R_2$ are methyl and between about 50 and 85 weight % when $R_1$ and $R_2$ are ethyl and the remaining portion of said mixture is essentially said N-monoalkylaminoethylbenzoate.

2. The composition of claim 1 wherein $R_1$ and $R_2$ are methyl in the N,N-dialkylamino ethyl benzoate portion and $R_1$ is methyl and $R_2$ is hydrogen in the N-monoalkylamino ethylbenzoate portion of a bi-component mixture.

3. The composition of claim 2 wherein the N,N-dimethylamino ethyl benzoate portion of the mixture is between 40 and 50 weight %.

4. The composition of claim 1 wherein $R_1$ and $R_2$ are ethyl in the N,N-dialkylamino ethylbenzoate portion and $R_1$ is ethyl and $R_2$ is hydrogen in the N-monoalkylamino ethyl benzoate portion of a bi-component mixture.

5. The composition of claim 4 wherein the N,N-diethylamino ethylbenzoate portion of the mixture is between 75 and 85 weight %.

6. The composition of claim 1 wherein between about 0.5 and about 12 weight % of the composition comprises said mixture of N-monoalkylamino and N,N-dialkylamino ethylbenzoates.

7. The composition of claim 6 wherein between about 1 and about 5 weight % of the composition comprises said mixture.

8. The composition of claim 1 wherein said mixture comprises the N,N-diethylamino ethylbenzoate/N-ethylamino ethylbenzoate mixture containing up to 30 weight % of N,N-dimethylamino ethylbenzoate/N-monomethylamino ethylbenzoate mixture based on the total benzoate mixture.

9. The composition of claim 1 wherein a mixture of 50 to 85 weight % of N,N-diethylamino ethylbenzoate and 50 to 15 weight % of N-ethylamino ethylbenzoate is intermixed with 0 to 50 weight % of a mixture of 25 to 50 weight % of N,N-dimethylamino ethylbenzoate and 75 to 50 weight % of N-methylamino ethylbenzoate.

10. The composition of claim 1 wherein the composition contains an antioxidant.

11. The composition of claim 10 wherein antioxidant is present in an amount between about 0.1 and about 8 weight % based on total composition.

12. The composition of claim 1 wherein the carrier is an aqueous solution of an aliphatic alcohol containing two to four carbon atoms.

13. The composition of claim 1 wherein the carrier is a polyoxylated vegetable oil.

14. The composition of claim 1 wherein the carrier is an alcohol-glycerin mixture.

15. The composition of claim 1 wherein the carrier is a mixture of isopropyl stearate and polyoxyethylated sorbitan monopalmitate.

* * * * *